United States Patent [19]

Shaw

[11] Patent Number: 5,403,961
[45] Date of Patent: Apr. 4, 1995

[54] PRODUCTION OF POLYSULFIDES

[75] Inventor: James E. Shaw, Bartlesville, Okla.

[73] Assignee: Phillips Petroleum Company, Bartlesville, Okla.

[21] Appl. No.: 155,502

[22] Filed: Nov. 22, 1993

[51] Int. Cl.⁶ .................. C07C 319/28; C07C 319/26; C07C 319/22

[52] U.S. Cl. ...................................... 568/21; 568/19; 568/22; 568/24

[58] Field of Search ........................ 568/19, 21, 22, 24

[56] References Cited

U.S. PATENT DOCUMENTS

| | | | |
|---|---|---|---|
| 5,155,275 | 10/1992 | Shaw | 568/21 |
| 5,174,922 | 12/1992 | Perozzi et al. | 568/21 |
| 5,206,439 | 4/1993 | Shaw | 568/21 |
| 5,218,147 | 6/1993 | Shaw | 568/21 |

FOREIGN PATENT DOCUMENTS 76376  4/1983  European Pat. Off. ... C07C 149/12

Primary Examiner—Johann Richter
Assistant Examiner—Michael B. Hydorn
Attorney, Agent, or Firm—Lucas K. Shay

[57] ABSTRACT

A process for preparing a stabilized and deodorized organic polysulfide compound is provided which comprises contacting a crude polysulfide, in the presence of a solvent, optionally further in the presence of a basic compound, with a metal salt of an inorganic acid or a metal salt of an organic acid under conditions sufficient to produce the stabilized and deodorized polysulfide.

36 Claims, No Drawings

PRODUCTION OF POLYSULFIDES

FIELD OF THE INVENTION

The present invention relates to a process for producing a stable polysulfide,

BACKGROUND OF THE INVENTION

Organic polysulfides and particularly dialkyl polysulfides such as tetra- and penta-sulfides have been found useful for many purposes such as additives or elastomers, antioxidants for lubricating oils, intermediates for the production of organic chemicals, insecticides, germicides and as an additive to diesel fuels to improve the cetane number and ignition qualities of these fuels. These compounds have also found useful in the compounding of extreme pressure lubricants and in the acceleration of rubber treating processes.

Such polysulfide compounds can be prepared by reacting mercaptans with elemental sulfur in the presence of a basic catalyst. For example, Biensan et al (U.S. Pat. No. 3,308,166) discloses that polysulfides can be prepared from a mercaptan and sulfur catalyst by an amine using an alcohol promoter.

A conventional process for producing a polysulfide compound such as di-t-dodecyl polysulfide is to react a mercaptan such as t-dodecylmercaptan with elemental sulfur in the presence of a catalyst. However, the polysulfide thus prepared is associated with some unreacted mercaptans and residual H$_2$S contributing to unpleasant odor. Additionally, possibly because of the unreacted mercaptans, the product always becomes very unstable, i.e., the product turns cloudy, probably due to degradation of the polysulfide causing precipitation of sulfur. The instability along with the unpleasant odor greatly reduce the desirability and utility of the polysulfide product.

There is therefore a need to remove the odor associated with the product and to stabilize the product. For example, European Patent Application 76 376 (Apr. 4, 1993) discloses that a newly synthesized crude polysulfide can be deodorized by treating the crude polysulfide with a metal salt of an inorganic or organic acid at an elevated temperature. However, the process disclosed therein requires a lengthy treatment in order to obtain a satisfactory result. The reference process also discloses that powdered an hydrous salt is preferred. Powdered anhydrous salt generally is more expensive than a hydrate salt and requires additional processing cost for producing the powdered form. It would therefore be a significant contribution to the art to develop an improved process for the stabilization and deodorization of a crude polysulfide product so that the product is made more useful for industrial uses.

SUMMARY OF THE INVENTION

An object of the present invention is to develop a process to stabilize a polysulfide compound. Another object of the present invention is to reduce the odor associated with the polysulfide compound. A further object of the present invention is to reduce unreacted or residual sulfur-containing compounds contaminating the polysulfide. Yet another object of the present invention is to prepare a polysulfide that is stable and deodorized.

An advantage of the present invention is the reduction in the concentration of the unreacted mercaptans to reduce odor and to produce a stable product yet maintaining the polysulfide in high yield. Additionally, the process of the invention requires less salt than the referenced process meaning reduced cost for treatment of crude polysulfide and for disposal of the metal salt. Other advantages and features will become more apparent as the invention is more fully disclosed in the following disclosure and claims.

According to the present invention, a process for stabilizing and deodorizing a crude polysulfide is provided which comprises contacting the crude polysulfide with, in the presence of a solvent, a metal salt of an inorgan or organic acid.

DETAILED DESCRIPTION OF THE INVENTION

According to the present invention, the process for preparing a stabilized and deodorized polysulfide compound comprises contacting a crude polysulfide, in the presence of a solvent, with a metal salt of an acid. The solvent suitable for use in the invention is at least partially soluble in water and the acid can be an inorganic acid or an organic acid.

The term "stabilized and deodorized" used herein generally refer to a polysulfide compound having a mercaptan sulfur content of less than 30 ppm by weight, or having a clear color, or both, after at least one month of storage at about 20°–30° C. The term "partially soluble" is used herein to refer to a solubility of about 5 weight % to complete miscibility at about 10°–30° C. The term "crude polysulfide" is a polysulfide compound produced by catalyzed reaction of a mercaptan and sulfur, without any further treatment. Generally any crude polysulfide can be used in the practice of the present invention.

The crude polysulfide useful in the present invention has a general formula of RS$_n$R' with R and R' can be the same or different and are alkyl radicals having about 1 to about 20 carbon atoms, and n is an integer of 2 to 10. Preferably R and R' are alkyl radicals having about 3 to about 15 carbon atoms and n is 3 to 8. Most preferably, R and R' are alkyl radicals having 9 to 12 carbon atoms and n is 3 to 6. R and R' can also bear substituents such as halo, hydroxy, and alkoxy substituents.

The crude polysulfide can be prepared by the reaction of mercaptans and elemental sulfur catalyzed by a basic catalyst. The reaction is depicted as RSH+R'SH+(n−1)S→RS$_n$R'+H$_2$S where R,R' and n are the same as those described above. The reaction can be carried out under any reaction condition, in any suitable reaction vessel. The basic catalyst can be a metal hydroxide such as sodium hydroxide, a metal oxide or a metal salt such as MgO and NaCO$_3$ an an amine such as triethylamine. Generally, one of the reactants, either the mercaptan or sulfur, is slowly added to the other reactant in the presence of a basic catalyst. The sulfur, upon addition, readily dissolves in the solution. Mixing of the solution and/or operating at higher than ambient temperatures will enhance the reaction rate. The amount of sulfur added depends on the desired sulfur content of polysulfide product. For an average sulfur content of n-sulfurs per polysulfide molecule, (n−1) moles of sulfur must be added and 1 mole of hydrogen sulfide will be released per 2 moles of mercaptans reacted. The weight of the basic catalyst as a percentage of the weight of mercaptan should be 0.05 to 5%, preferably 0.1 to 2.0%, and most preferably 0.2 to 1.0%.

Following completion of the reaction, residual hydrogen sulfide may be removed from the crude polysulfide product by either an inert gas purge or by vacuum stripping. When using an inert gas purge, preferably gases are nitrogen and air.

The crude polysulfide is then contacted, in the presence of a solvent, with a metal salt of an inorganic or organic acid. Suitable solvents are generally partially soluble in water such as ethers, alcohols, and ketones. Examples of suitable solvents include, but are not limited to, water, methanol, ethanol, propanol, acetone, methyl ethyl ketone, tetrahydrofan, and other similar oxygen-containing solvents. Methanol is the presently preferred solvent because of its combined solubilization properties and high vapor pressure. The presently most preferred solvent comprises water and one of the solvents illustrated above.

The metal salt of inorganic acid is also generally partially soluble in water. The cation moiety of the metal salt selected from the group consisting of cobalt, cadmium, copper, iron, lead, manganese, mercury, nickel, silver, zinc, and combinations of two or more thereof. The anion moiety of the metal salt is selected from the group consisting of borate, bromide, carbonate, chloride, fluoride, iodide, nitrate, nitrite, phosphate, sulfate, and combinations of two or more thereof. The presently preferred metal salts of inorganic acids are iron sulfate, copper sulfate, and zinc sulfate.

The scope of the cation moiety of the metal salt of organic acid is the same as that disclosed above for the metal salt of inorganic acid. The anion moiety of the metal salt of organic acid is selected from the group consisting of $C_1$-$C_{20}$ carboxylic acid, preferably saturated monocarboxylic acid. Examples of suitable organic acid moiety include, but are not limited to, formate, acetate, propionate, butyrate, caprylate, laurate, palmitate, stearate, and combinations of two or more thereof. The presently preferred metal salt of organic acid is copper acetate.

According to the present invention, the molar ratio of the metal salt to the crude polysulfide is generally in the range of from about 0.00001:1 to about 1:1, preferably about 0.0001:1 to about 0.1:1, and most preferably 0.001:1 to 0.02:1. The molar ratio of the solvent to the crude polysulfide is generally in the range of from about 0.001:1 to about 10:1, preferably about 0.01:1 to about 1:1, and most preferably 0.1:1 to 0.5:1.

The process of the invention can be carried out under a wide range of pressure. Generally it is carried out at atmospheric pressure and can be higher or lower. It can be in the range of from about 0.5 to about 100 atmospheres (arm), preferably from about 0.5 to about 10 arm, and most preferably 0.9 to 1.1 arm. The time required to complete the treatment generally depends on the amount of the metal salt used. Generally it takes about 10 minutes to about 5 hours to complete. The process can be carried out at various temperature ranges. Generally the process is in the range of from about 20° to about 100° C., preferably about 30° to about 80° C., and most preferably 40° to 60° C..

The process of the invention can also be carried out by contemporaneous agitation of the process medium which contains the crude polysulfide and the metal salt. Any agitation means can be used. For example, mechanic stirring, air sparging, are suitable means.

According the the invention, the process can also be carried out in the presence of a basic compound. Generally, the basic compound is partially soluble in the water and organic solvent. The basic compound can be an inorganic base or an organic base and in a solid phase or a liquid phase.

The basic compound useful in the present invention can be employed as it is, supported on a solid support such as all forms of alumina and silica, or an aqueous solution. The presently preferred basic inorganic compound is selected from the group consisting of LiOH, NaOH, KOH, $Ca(OH)_2$, $Mg(OH)_2$, $Na_2O$, MgO, CaO, $NaHCO_3$, $Na_2CO_3$, $CaCO_3$, and mixtures thereof. The presently most preferred base is NaOH because of its availability and cost.

The presently preferred organic base is a tetraalkylammonium hydroxide, including tetramethylammonium hydroxide, tetraethylammonium hydroxide, tetrapropylammonium hydroxide, and combinations of two or more thereof. The presently most referred tetraalkylammonium hydroxide is tetramethylammonium hydroxide.

If the basic compound is present, the molar ratio of the basic compound to the crude polysulfide is from about 0.001:1 to about 2:1, preferably from about 0.005: to about 1:1, and most preferably from 0.01:1 to 0.1:1.

The process of the invention can be carried out in any suitable vessel. It is preferred to carry out in the same vessel where the crude polysulfide is prepared. Generally, the crude polysulfide is added to the basic compound and the solvent for further treatment. Though the basic compound and time solvent can also be separately added to the crude polysulfide, it is preferred that the basic compound be first mixed with a solvent, as described above, followed by being contacted with the crude polysulfide.

The treated mixture can be further purified if desired. This is usually done by conventional separation means such as filtration or by distillation to remove any impurities.

The process of the invention can also be carried out continuously. For example, the contacting of the metal salt, in a solvent, with the crude polysulfide can be done by employing continuous stir tank reactors connected in series, packed columns or towers in which the metal salt and solvent are supported on a solid support, and other continuous flows that are readily within the realm of one skilled in the art.

The following examples are provided to further illustrate the practice of the invention and are not intended to limit the scope of the invention or the claims.

EXAMPLE I

This example illustrates a process for preparing a crude dialkyl polysulfide having an average of 5 sulfurs.

To a 1 liter autoclave reactor which has been flushed with nitrogen (N2), it was added a solution of 599 g (3.74 mole) t-nonyl mercaptan and 3.8 g (0.037 mole) triethylamine. The autoclave was heated to 30° C. and the contents were stirred rapidly (1000 rpm). Sulfur (240 g, 7.49 mole) in a 300 ml stainless steel bomb equipped with an internal thermocouple was melted by heating at 120°-135° C. under $N_2$. With the melted sulfur at 135° C., the $N_2$ pressure above the sulfur in the bomb was increased to 200 psi, and the valve and tubing between the bomb and autoclave were heated so sulfur would not solidify in them during the sulfur transfer. The liquid sulfur was added over a 2 minute time period so as to avoid solidification of sulfur in the tube that went through the autoclave body. The Addition of the liquid sulfur over a 2 minute time period caused the autoclave temperature to increase from 30° C. to the desired process temperature of 45° C.

When the sulfur addition was completed, the autoclave pressure had increased to 150 psig due to $H_2S$ evolution. The autoclave pressure was then decreased to 60 psig by the controlled venting of $H_2S$ for about 0.5 hour. At this point, $H_2S$ was removed by pressurizing the autoclave with $N_2$ to 100 psi and then venting to 60 psig. This was repeated 3 more times over a 0.5 hour time period and the pressure (mainly due to $N_2$) was allowed to decrease near atmospheric whereupon the system was opened to a vent line. Heating at 45° C. with rapid stirring (1000 rpm) was continued for an additional 1.5 hours (total time after addition of all sulfur was 2.5 hours). Nitrogen was then bubbled (2 std cubic ft/hr) through the reaction mixture at 45° C. with rapid stirring (1000 rpm) for 4 hours to remove most (but not all) hydrogen sulfide and triethylamine.

The crude t-nonyl polysulfide thus prepared generally contained about 50 to about 300 ppm (by weight) of mercaptan sulfur. The mercaptan sulfur content was determined by potentiometric titration using mercuric perchlorate.

EXAMPLE II

This example illustrates another process for preparing a crude polysulfide.

To a 2 liter 3-neck flask equipped with condenser, thermowell, and magnetic stir bar, it was added 721 g (4.5 mole) of t-nonyl mercaptan and 4.5 g (0.044 mole) of triethylamine to form a solution. The solution was heated to 45° C. followed by adding 289 g (9.0 mole) of sulfur (sublimed or flowers of sulfur) in small portions over 45 minutes at 45° C. Hydrogen sulfide was evolved during this addition. The solution was further heated with stirring at 45° C. for an additional 2.5 hours. Then a gas dispersion tube was placed in the solution and nitrogen gas was bubbled through the solution (approximately 2 standard cubic ft/hr) with stirring for 4 hours at 45° C. The crude t-nonyl polysulfide thus prepared contained 50–300 ppm mercaptan sulfur.

EXAMPLE III

This example illustrates the invention process for producing a stabilized polysulfide.

A mixture of zinc sulfate heptahydrate (0.5 g), NaOH in methanol solution (1.0 g; the NaOH-methanol solution was prepared by mixing 20 g of 50% NaOH solution and 40 g of methanol), water (2 g), and methanol (4 g) was added to a 500 ml, 3-neck flask equipped with a thermawell, a magnetic stir bar, and a condenser with $N_2$ inlet on top. One hundred seventy-four grams of crude t-nonyl polysulfide, as produced in Example II were then added to the flask. The content of flask was then heated for 2.5 hours at 50° C. with stirring followed by vigorous nitrogen sparging at 50° C. for 1.5 hours. The treated t-nonyl polysulfide was then recovered by filtering through a filter paper to give clear yellow liquid t-nonyl polysulfide. The mercaptan sulfur content of the stabilized and deodorized t-nonyl polysulfide was less than the detection limit of about 1 ppm. After 7 months, the treated polysulfide was still clear and yellow.

EXAMPLE IV

This example demonstrates that a stable polysulfide can be produced by treating a crude polysulfide with a metal salt of a carboxylic acid in the presence of a solvent.

One hundred seventy-four grams of t-nonyl mercaptan, prepared by the method of Example II, were added to the flask described in Example III wherein the flask already contained a mixture containing copper(II) acetate monohydrate (0.5 g), water (1.5 g) and methanol (3.0 g). The content of the flask was then heated for 2 hours at 50° C. followed by vigorous sparging with nitrogen gas for 1.5 hours. The treated mixture was filtered through a filter paper to obtain a clear, yellow t-nonyl polysulfide. The mercaptan sulfur content of the stabilized and deodorized t-nonyl polysulfide was less than detection limit of about 1 ppm by weight. The product remained clear and yellow with no precipitate after being aged for about 7 months.

EXAMPLE V

This example illustrates the preparation of a stabilized and deodorized polysulfide by treatment with copper sulfate.

The runs were carried out by first adding 1.50 g of t-nonyl polysulfide, prepared by the method of Example II, to a flask described in Example III. A copper(II) sulfate solution (quantity noted in Table I below) which was prepared by dissolving 7.4 g of copper(II) sulfate pentahydrate in 25 g of water was added to the flask. Also, 3.0 g methanol (if present, see Table I) was added to the flask. The content in the flask was heated at 50° C. for 2.5 hours followed by vigorous nitrogen sparging at 50° C. for 1.5 hours. After the content was cooled to about 25° C., it was filtered through a filter paper to obtain clear, yellow t-nonyl polysulfide. The results are shown in Table I below.

TABLE I

| | Copper Sulfate-treated t-nonyl Polysulfide | | | |
|---|---|---|---|---|
| Run | $CuSO_4$ (g) | Methanol (g) | Mercaptan Sulfur (ppm) | Clarity, Color & Stability |
| 1 | 2.30[a] | 3.0 | 21 | clear, yellow, 3 months |
| 2 | 3.80[a] | 3.0 | 16 | clear, yellow, 3 months |
| 3[b] | 1.62[a] | — | 244 | slightly hazy, precipitate 2 weeks |
| 4 | 2.43[a] | — | 177 | slightly hazy, slight precipitate, 3 weeks |
| 5[c] | 0.75[c] | — | 12–17 | clear, yellow 7 months |

[a]Copper sulfate solution, 14.6% by weight.
[b]Heating was done at 65° C.
[c]Control run. Solid, powdered, anhydrous copper sulfate was used in this control run. Heating was done at 65° C. for 4 hours.

The results shown in Table I indicate that in the presence of a solvent (methanol, runs 1–2), a short heating time of 2.5 hours and less than 0.34 g of copper sulfate was required to obtain a stabilized t-nonyl polysulfide. Disposal of copper sulfate causes environmental concern. For comparison, the control run (run 5) required a much longer time of treatment and more than twice that of copper sulfate to achieve a similar result. Comparing runs 1–2 to runs 3–4, it is clear that in addition to water, the presence of a solvent (methanol) greatly improved the process.

The results shown in the above examples clearly demonstrate that the present invention is well adapted to carry out the objects and attain the ends and advantages mentioned as well as those inherent therein. While That which is claimed is:

1. A process comprising contacting a crude polysulfide compound, in the presence of a solvent, with a metal salt under conditions sufficient to produce a stabilized and deodorized polysulfide wherein said solvent is partially soluble in water and said metal salt is selected from the group consisting of a metal salt of inorganic acid and a metal salt of organic acid, or combinations of two or more thereof wherein the cation moiety of said metal salt of inorganic acid and organic acid is selected from the group consisting of cobalt, cadmium, copper, iron, lead, manganese, mercury, nickel, silver, and zinc, or combinations of two or more thereof; the anion moiety of said metal salt of inorganic acid is selected from the group consisting of borate, bromide, carbonate, chloride, fluoride, iodide, nitrate, nitrite, phosphate, and sulfate, or combinations of two or more thereof; and said organic acid is a $C_1$–$C_{20}$ carboxylic acid, and combinations of two or more thereof.

2. A process according to claim 1 wherein said polysulfide is a dialkyl polysulfide having the formula of $RS_nR'$ wherein R and R' are the same or different and each is an alkyl radical having about 1 to about 20 carbon atoms; and n is an integer of 2 to 10.

3. A process according to claim 2 wherein said alkyl radical has a substituent selected from the group consisting of halo radicals, hydroxy radicals, and alkoxy radicals, or combinations of two or more thereof.

4. A process according to claim 2 wherein each R and R' has about 3 to about 15 carbon atoms and n is 3 to 8.

5. A process according to claim 4 wherein each R and R' has 9 to 12 carbon atoms and n is 3 to 8.

6. A process according to claim 1 wherein said polysulfide is t-nonyl polysulfide.

7. A process according to claim 1 wherein said solvent is selected from the group consisting of methanol, ethanol, propanal, acetone, methyl ethyl ketone, and tetrahydrofuran, or mixtures thereof.

8. A process according to claim 1 wherein said solvent further comprises water.

9. A process according to claim 7 wherein said solvent is methanol.

10. A process according to claim 8 wherein said solvent is methanol.

11. A process according to claim 1 wherein the cation moiety of said metal salt of inorganic acid is selected from the group consisting of copper, and zinc, or combinations thereof.

12. A process according to claim 1 wherein the onion moiety of said metal salt of inorganic acid is sulfate.

13. A process according to claim 1 wherein said metal salt of inorganic acid is selected from the group consisting of copper sulfate, copper sulfate pentahydrate, zinc sulfate, and zinc sulfate heptahydrate, or combination thereof.

14. A process according to claim 1 wherein said metal salt of inorganic acid is copper(II) sulfate pentahydrate.

15. A process according to claim 1 wherein said metal salt of inorganic acid is zinc sulfate heptahydrate.

16. A process according to claim 1 wherein the cation moiety of said metal salt of organic acid is copper.

17. A process according to claim 1 wherein the anion moiety of said metal salt of organic acid is selected from the group consisting of formate, acetate, propionate, butyrate, caprylate, laurate, palmitate, and stearate, or combinations of two or more thereof.

18. A process according to claim 17 wherein said anion moiety is selected from the group consisting of formate, acetate, and propionate, or combinations of two or more thereof.

19. A process according to claim 18 wherein said anion moiety is acetate.

20. A process according to claim 1 wherein said metal salt of organic acid is copper(II) acetate.

21. A process according to claim 1 wherein the molar ratio of said metal salt to said crude polysulfide is in the range of from about 0.00001:1 to about 1:1.

22. A process according to claim 21 wherein said range is from 0.001 to 0.02:1.

23. A process according to claim 1 wherein the molar ratio of said solvent to said crude polysulfide is in the range of from about 0.00 1 to about 10:1.

24. A process according to claim 23 wherein said range is from 0.1:1 to 0.5:1.

25. A process according to claim 1 wherein said process is carried out in the presence of a basic compound.

26. A process according to claim 25 wherein said basic compound is selected from the group consisting of LiOH, NaOH, KOH, $Ca(OH)_2$, $Mg(OH)_2$, $Na_2O$, MgO, CaO, $NaHCO_3$, $Na_2CO_3$, $CaCO_3$, tetramethylammonium hydroxide, tetraethylammonium hydroxide, and tetrapropylammonium hydroxide, or combinations of two or more thereof.

27. A process according to claim 25 wherein said basic compound NaOH.

28. A process according to claim 25 wherein the molar ratio of said basic compound to said crude polysulfide is in the range of from about 0.00 1: 1 to about 2:1.

29. A process according to claim 28 wherein said range is from 0.01: to 0.1:1.

30. A process for stabilizing and deodorizing a crude polysulfide comprising contacting said crude polysulfide, in the presence of a solvent, with a metal salt under conditions sufficient to produce a stabilized and deodorized polysulfide wherein:
said crude polysulfide is a dialkyl polysulfide having the formula of $RS_nR'$ wherein each R and R'' is an alkyl radical having about 3 to about 15 carbon atoms and n is an integer of 3 to 8;
said solvent is selected from the group consisting of water, methanol, ethanol, acetone, methyl ethyl ketone, and tetrahydrofuran, or combinations of two or more thereof; and
said metal of said metal salt is selected from the group consisting of cobalt, cadmium, copper, iron, lead, manganese, mercury, nickel, silver, and zinc, or combinations of two or more thereof; said metal salt has an anion moiety selected from the group consisting of an inorganic acid, and an organic acid, or combinations thereof wherein said inorganic acid is selected from the group consisting of borate, bromide, carbonate, chloride, fluoride, iodide, nitrate, nitrite, phosphate, and sulfate, or combinations of two or more thereof, and said organic acid is a $C_1$–$C_{20}$ carboxylic acid.

31. A process according to claim 30 wherein said crude polysulfide is t-nonyl polysulfide; said solvent is selected from the group consisting of water, and methanol, or mixture thereof; said metal salt is selected from tie group consisting of copper sulfate, zinc sulfate, and copper acetate or hydrates thereof, or combinations of two or more thereof.

32. A process for stabilizing and deodorizing a crude polysulfide, in the presence of a solvent and a basic compound, with a metal salt under conditions sufficient to produce a stabilized and deodorized polysulfide wherein:

said crude polysulfide is a dialkyl polysulfide having the formula of $RS_2R'$ wherein each R and R" is an alkyl radical having about 3 to about 15 carbon atoms and n is an integer of 3 to 8;

said solvent is selected from the group consisting of water, methanol, ethanol, propanel, acetone, methyl ethyl ketone, and tetrahydrofuran, or mixtures thereof;

said basic compound is selected from the group consisting of LiOH, NaOH, KOH, $Ca(OH)_2$, $Mg(OH)_2$, $Na_2O$, MgO, CaO, $NaHCO_3$, $Na_2CO_3$, $CaCO_3$, tetramethylammonium hydroxide, tetraethylammonium hydroxide, and tetrapropylammonium hydroxide, or combinations of two or more thereof; and said metal of said metal salt is selected from the group consisting of cobalt, cadmium, copper, iron, lead, manganese, mercury, nickel, silver, and zinc, or combinations of two or more thereof; wherein said metal salt has an anion moiety selected from the group consisting of an inorganic acid, and an organic acid, or combinations thereof wherein said inorganic acid is selected from the group consisting of borate, bromide, carbonate, chloride, fluoride, iodide, nitrate, nitrite, phosphate, and sulfate, or combinations of two or more thereof, and said organic acid is a $C_1$–$C_{20}$ carboxylic acid.

33. A process according to claim 32 wherein said crude polysulfide is t-nonyl polysulfide; said solvent is selected from the group consisting of water, and methanol, or mixture thereof; said basic compound is NaOH; said metal salt is selected from the group consisting of copper sulfate, zinc sulfate, and copper acetate, or hydrates thereof, or combinations of two or more thereof.

34. A process according to claim 33 wherein said metal salt is copper sulfate.

35. A process according to claim 33 wherein said metal salt is zinc sulfate.

36. A process according to claim 33 wherein said metal salt is copper(II) acetate.

* * * * *